United States Patent

Shukla et al.

[11] Patent Number: 6,028,525
[45] Date of Patent: Feb. 22, 2000

[54] WIRELESS LEVEL SWITCH

[76] Inventors: Ashok K Shukla; Mukta M Shukla, both of 10423 Popkins Ct., Woodstock, Md. 21163

[21] Appl. No.: 09/033,692

[22] Filed: Mar. 3, 1998

[51] Int. Cl.[7] ................................................. G08B 21/00

[52] U.S. Cl. .................. 340/689; 340/691.1; 340/693.1; 340/571; 340/539

[58] Field of Search ................................ 340/689, 686.1, 340/691.1, 692, 693.1, 571, 539

[56] References Cited

U.S. PATENT DOCUMENTS

| 4,547,972 | 10/1985 | Heidel et al. | 33/366 |
|---|---|---|---|
| 5,661,464 | 8/1997 | Bilak et al. | 340/690 |
| 5,801,618 | 9/1998 | Jenkins | 340/426 |
| 5,877,686 | 3/1999 | Ibey et al. | 340/571 |

Primary Examiner—Nina Tong

[57] ABSTRACT

This invention relates to a tilt switch, which when activated sends signals to a wireless remote receiver. The receiver will alert the human operator and/or execute a process or any programmed action.

7 Claims, 2 Drawing Sheets

WIRELESS LEVEL SWITCH

FIELD OF THE INVENTION

This invention relates to a tilt switch for ON/OFF applications. Once the switch is activated, it sends signals to a wireless receiver for warning or to execute an action or process.

BACKGROUND OF INVENTION

In this invention, we describe the simple wireless tilt switch, which gets activated once the angle of the switch is changed. Once this switch is activated, it sends signals to a wireless remote receiver for the execution of an action or process.

There are many situations in which once the tilt switch is activated(primary action), a secondary action is required. The secondary action (for example starting or stopping of a pump, recorder or any other device) is taken by an operator. Here a transmitter is used which gets activated once the primary action takes place and sends signals to a receiver for the secondary action.

For example, in liquid chromatography, an injection valve is used for applying the sample to the separation column. The injection valve is filled with the sample and the sample is injected into the column by moving a handle. As soon as the sample is injected, it is required that the recorder be activated simultaneously to record the data. There are some injection valves available for simultaneous switching of the recorder but these can only be connected by means of wiring to the recorder or other devices. In the invention described here, no wires are needed and at the same time more than one process can be controlled and/or executed.

Similarly, there are door alarms available, which get activated by the vibration or movement of the door. The device itself produces sound or light. However, if a person is far away from the alarm system, he can not hear or see the alarm. If a wireless transmitter is built into the tilt switch, it can transmit the alarm to a wireless remote receiver, which can be virtually put in different places. The advantage of this system is that it can be used in any place without tedious wiring connections.

The invention described and claimed herein comprises a levelness sensor (for example, a tilt switch), with a built-in transmitter, which on activation sends signals to a receiver for alarm or for executing an action or process.

This tilt or vibration switch can have many applications in the research lab, industry as well as in the consumer market for our day to day lives. The advantage of this device is its simplicity in use, safety and reliability.

The various features of novelty which characterize the invention are pointed out with particularity in the claims annexed to and forming a part of this disclosure. For a better understanding of the invention, its advantages and objects, reference is made to the accompanying drawings and descriptive matter in which a preferred embodiment of the invention is illustrated.

BRIEF DESCRIPTION OF THE DRAWINGS

The foregoing and still other objects of this invention will become apparent, along with various advantages and features of novelty residing in the present embodiments, from study of the following drawings, in which.

DESCRIPTION OF THE PREFERRED EMBODIMENT

Figure 1:
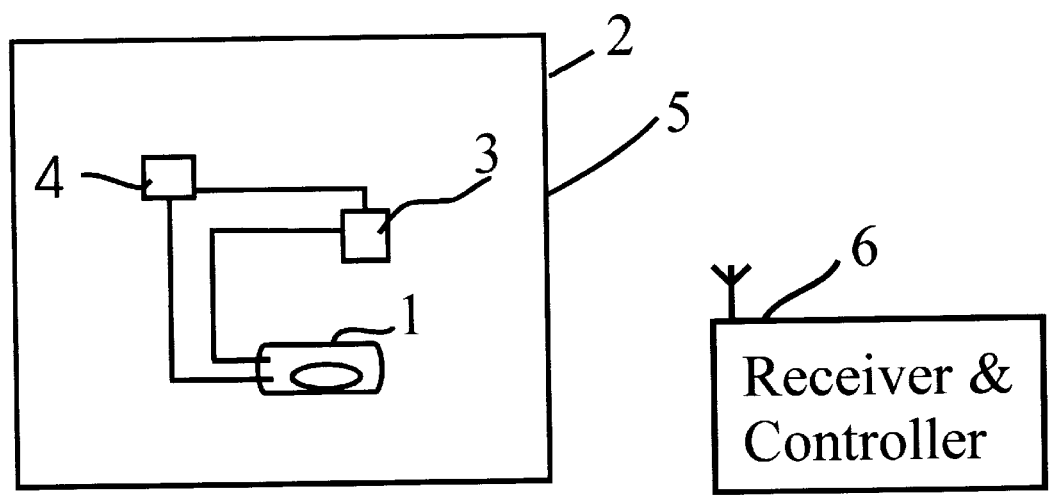
FIG. 1 is an expanded view of one embodiment of a device according to present invention.
Figure 2:
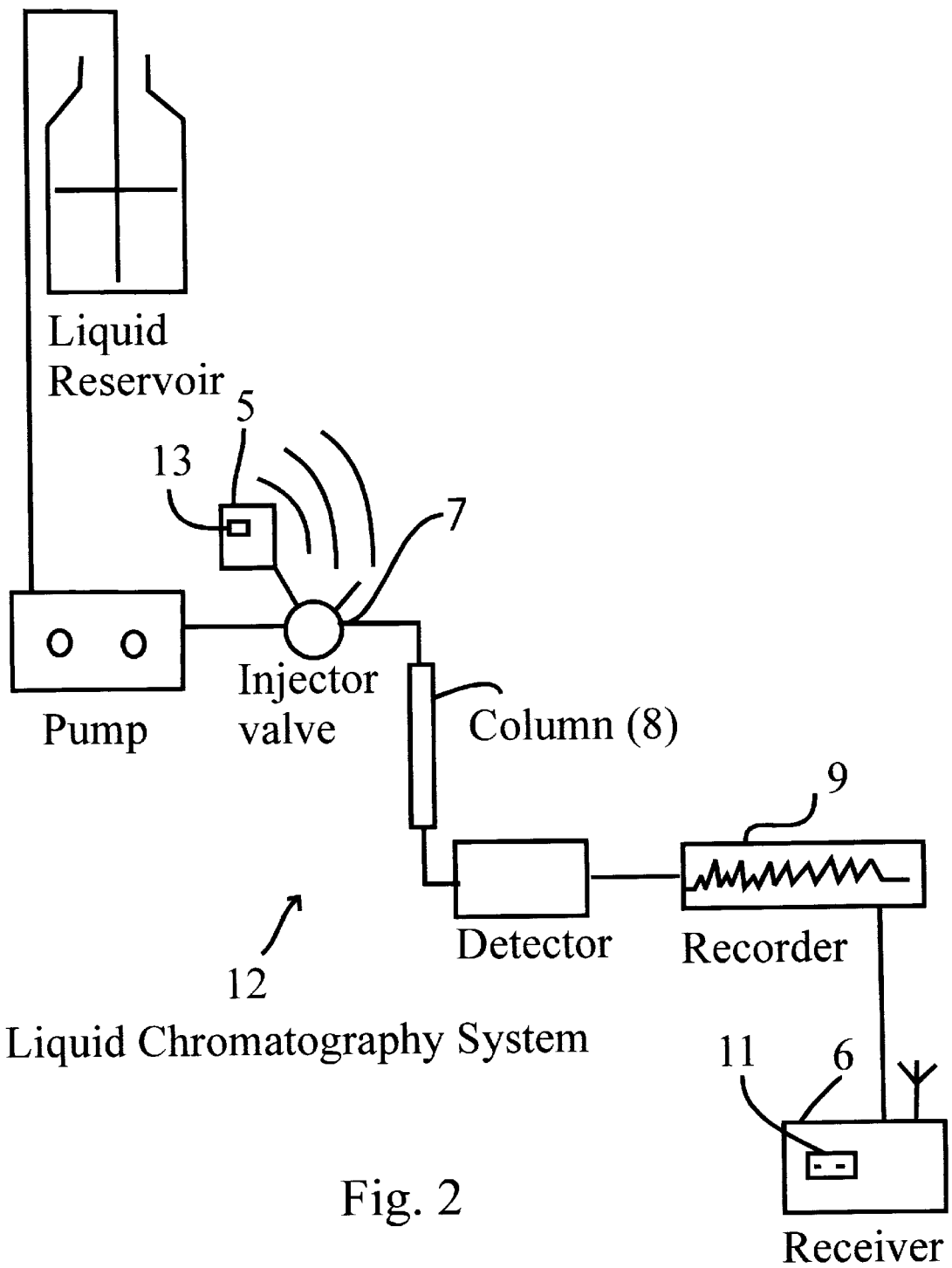
FIG. 2 is a liquid chromatography injection valve system with a levelness sensing means.

Referring to the drawings, the invention is a levelness sensor (1)(for example, a mercury switch) inside a device (2). The device can be made of any material and coupled to an alarm device (3) (such as an audible alarm, a radio frequency or light emitting diode, ultrasound, infrared diodes and UV-light), powered by a battery (4) in series with a tilt switch (1) in a case (5) shown in overview in FIG. 1.

Referring to the FIG. 1, the invention is embodied in such a way that the device gets activated at a desired angle and sends an alarm. The device can be activated either manually or automatically.

The alarm could be a light source (for example. A light emitting diode), sound source (beeper), a transmitter or a transreceiver (for frequency generation). The transmitter(3) or transreceiver will send signals to the receiver or to a transreceiver. Once the receiver gets signals from the transmitter, it will warn or alarm the human operator by producing signals like light, sound or both. The receiver can also be coupled with a timer so as to take automatic remedial action if a human operator does not intervene within a predetermined time period.

Transreceivers are devices that work as transmitters as well as receivers. The transmitter and the receiver in the device can be each replaced by a transreceiver. The advantage in using a transreceiver is that the communication between the sender(level sensor) and the receiver is both ways i.e. either can receive or send signals.

In the device 1, the transmitter can also be replaced by a transponder which can work without a battery.

In device (2) an inclinometer coupled to a switch can replace the tilt switch. The advantage of using inclinometer is that a very precise angle can be preset for the activation of alarm.

Furthermore, a switch can be incorporated in the electronic circuit for the activation or deactivation of the battery during the transport or storage. Further the circuit has the possibility to deactivate after sending the signal and thus save the life of the battery.

The device can also have other sensors (13) like smoke detector, levelness sensor, gas detector, solvent leakage detector, temperature sensor, and conductive detector for wetness along with the tilt switch.

One transmitter can send signals to many receivers and/ or one receiver can receive signals from different transmitters.

The broader usefulness of the invention may be illustrated by the following examples.

EXAMPLE #1

High Performance Liquid Chromatography (HPLC) Switching Valve

A liquid chromatography injection valve system (12) comprises a liquid chromatography, an injection valve is used for applying the sample to the separation column. The injection valve is filled with the sample and then the sample is injected to the separation column (8) by moving a handle. As soon as the sample is injected, it is important to start the recorder (9) in order to get the data recorded simultaneously. Up to now, the recorder switch is pressed either manually or by using an injection valve which has a built-in switch with wiring connections to the recorder or control device. The receiver (6) may having a delay switch (11).

The wireless switch described in this invention does not require wiring and the receiver can be directly attached to the recorder or other devices (for example auto sampler or recorder). Furthermore, the device can send signals to different receivers for simultaneous action (for example, autosampler, recorder).

EXAMPLE #2
Door Alarm System

The wireless tilt switch device can be hung or built in a door handle or garage door. As soon as the door or the handle is moved, the tilt switch is activated and sends an alarm to the receiver for warning or executing a process or action like switching on the lights, making a sound alarm and/or activating the central alarm system to warn and alert.

EXAMPLE #3
Industrial ON/OFF Switch

In industry there are many situations where different switches need to be activated and the activation recorded by other devices for further processing. This type of switch can be extremely useful in these situations.

EXAMPLE #4
Anti-Theft Alarm System

This tilt switch can be installed in any object such as computers, printers, photocopiers etc. as anti theft device to warn or alarm their removal from a certain place.

In suitcases or luggage, for example if a suitcase is lying somewhere and if the alarm is activated, the receiver will immediately warn the owner that the suitcase is being removed. The owner can switch off the alarm when the luggage is being carried by the owner to avoid a false alarm.

While a specific embodiment of the invention has been shown and described in detail to illustrate the application of the principles of the invention, it is understood that the invention may be embodied otherwise without departing from such principles and that various modifications, alternate constructions, and equivalents will occur to those skilled in the area given the benefit of this disclosure and the embodiment described herein, as defined by the appended claims.

What is claimed is:

1. A system for automatically starting a recorder or a control device in a liquid chromatography injection valve system to get the data recorded simultaneously or control the system simultaneously, which comprises:

a levelness sensing means is attached to a liquid chromatography injection valve which comprises a handle;

wherein said sensing means comprises a housing for housing a tilt switch, a wireless transmitter system, and a battery;

wherein said injection valve is filled with sample of the liquid;

wherein said sample is injected into a separation column by moving said handle;

wherein said tilt switch is coupled to the transmitter system and the battery such that the transmitter system is activated when said tilt switch reaches a desired angle upon the movement of the handle, and said transmitter system sends a unique coded signals to a wireless remote receiver as soon as the sample is injected and said handle is moved;

wherein said receiver is attached to the recorder or the control device;

wherein said recorder or the control device is activated after receiving said signals from the transmitter system for starting to record the data simultaneously or controlling the system simultaneously.

2. The system as in claim 1 wherein said tilt switch is an inclinometer switch.

3. The system as in claim 1 wherein said transmitter and system is a transreceiver.

4. The system as in claim 1 wherein said transmitter system is a transponder.

5. The system as in claim 1 wherein said signals are selected from at least one of a group consisting of light, infrared light, frequency, radio frequency, ultra sound, sound and 900 mega hertz.

6. The system as in claim 1 wherein said receiver has a delay switch.

7. The device in claim 1 can have other sensors like smoke detector, wetness sensor, gas sensors, and temperature sensors.

* * * * *